United States Patent
Hammer et al.

(10) Patent No.: US 10,076,622 B2
(45) Date of Patent: *Sep. 18, 2018

(54) SINGLE LUNG/LOBE VENTILATION ENDOTRACHEAL TUBE

(71) Applicants: Gregory Benson Hammer, Stanford, CA (US); Lawson Fisher, Portal Valley, CA (US); Ryan Braunstein, San Carlos, CA (US)

(72) Inventors: Gregory Benson Hammer, Stanford, CA (US); Lawson Fisher, Portal Valley, CA (US); Ryan Braunstein, San Carlos, CA (US)

(*) Notice: Subject to any disclaimer, the term of this patent is extended or adjusted under 35 U.S.C. 154(b) by 42 days.

This patent is subject to a terminal disclaimer.

(21) Appl. No.: 15/131,976

(22) Filed: Apr. 18, 2016

(65) Prior Publication Data
US 2016/0243326 A1    Aug. 25, 2016

Related U.S. Application Data

(63) Continuation-in-part of application No. 13/746,583, filed on Jan. 22, 2013, now Pat. No. 9,314,580.
(Continued)

(51) Int. Cl.
*A61M 16/04* (2006.01)

(52) U.S. Cl.
CPC .... *A61M 16/0404* (2014.02); *A61M 16/0434* (2013.01); *A61M 16/0459* (2014.02)

(58) Field of Classification Search
CPC .............. A61M 16/04; A61M 16/0402; A61M 16/0404; A61M 16/0427; A61M 16/0434;
(Continued)

(56) References Cited

U.S. PATENT DOCUMENTS 3,616,799 A * 11/1971 Sparks .................. A61M 16/04
                                                        128/207.15
4,166,468 A    9/1979 Haynie
(Continued)

FOREIGN PATENT DOCUMENTS

WO          99/65552 A1    12/1999
WO      2004/069289 A2     1/2004

OTHER PUBLICATIONS

Campbell; et al., "Manufacturing Defect in a Double-Lumen Tube", Anesthesia & Analgesia (1991), 73(6):825-826.
(Continued)

*Primary Examiner* — Jackie Tan-Uyen T Ho
*Assistant Examiner* — Joseph D Boecker
(74) *Attorney, Agent, or Firm* — Ascenda Law Group, PC

(57) ABSTRACT

Techniques for single lung ventilation (SLV) include a hollow main tube with outer diameter sized to fit inside a bronchus of a patient. The length of the main tube is sufficient for a distal end of the main tube to reach a first side bronchus from a proximal end configured to be located in a vicinity of a mouth of the patient. The hollow main tube has a ventilating orifice separated from the distal end at a location that corresponds to a different second side bronchus. A hollow tubular sleeve is moveably disposed inside and longitudinally aligned with the main tube. The sleeve is configured to be positioned in at least two positions: a first position that does not block the ventilating orifice; and, a second position that does block the ventilating orifice.

24 Claims, 13 Drawing Sheets

Related U.S. Application Data

(60) Provisional application No. 61/589,335, filed on Jan. 21, 2012.

(58) Field of Classification Search
CPC .......... A61M 16/0459; A61M 16/0475; A61M 16/0484; A61M 16/0488; A61M 2039/082; A61M 2210/1025–2210/1029
USPC ............ 128/200.24, 200.26, 203.12, 204.18, 128/207.14, 207.15; 600/529, 538, 560; 604/36
See application file for complete search history.

(56) References Cited

U.S. PATENT DOCUMENTS

| | | | |
|---|---|---|---|
| 4,233,984 A | 11/1980 | Walling | |
| 4,248,221 A | 2/1981 | Winnard | |
| 4,762,125 A | 8/1988 | Leiman et al. | |
| 4,827,925 A | 5/1989 | Vilasi | |
| 5,038,777 A | 8/1991 | Dunn | |
| 5,312,352 A | 5/1994 | Leschinsky et al. | |
| 5,315,992 A | 5/1994 | Dalton | |
| 7,121,280 B2 | 10/2006 | Kyle, Jr. | |
| 8,393,328 B2* | 3/2013 | Angel | A61M 16/04 128/200.26 |
| 9,314,580 B2* | 4/2016 | Hammer | A61M 16/0434 |
| 9,789,271 B2* | 10/2017 | Pol | A61B 1/00045 |
| 2002/0043266 A1 | 4/2002 | Toti et al. | |
| 2007/0208294 A1 | 9/2007 | Stone | |
| 2008/0156323 A1* | 7/2008 | Angel | A61M 16/04 128/200.26 |
| 2010/0106236 A1 | 4/2010 | Nelson | |
| 2012/0024292 A1 | 2/2012 | Sandmore et al. | |
| 2014/0076326 A1* | 3/2014 | Pol | A61B 1/00045 128/207.15 |

OTHER PUBLICATIONS

Hammer; et al., "The Univent tube for single lung ventilation in paediatric patients", Paediatric Anaesthesia (1998), 8 (1):55-51, Abstract Only, downloaded from: http://onlinelibrary.wiley.com/doi/10.1046/j.1460-9592.1998.00691.x/abstract, 9 pages.

Hammer; et al., "Single lung ventilation in children using a new paediatric bronchial blocker", Paediatric Anaesthesia (2002), 12(1):69-72.

Perel; et al., "Collapse of endotracheal tubes due to overinflation of high-compliance cuffs", Anesthesia & Analgesia (1977), 56(5):731-733.

Smiths Medical International Ltd., "Tracheal Tubes—A Guide to Size and Length", 2009, retrieved from www.smiths-medical.com/userfiles/trachealtubechart.pdf, 1 page.

Taylor; et al., "Pediatric Cuffed Endotracheal Tubes: An Evolution of Care", The Ochsner Journal (2011), 11:52-56.

* cited by examiner

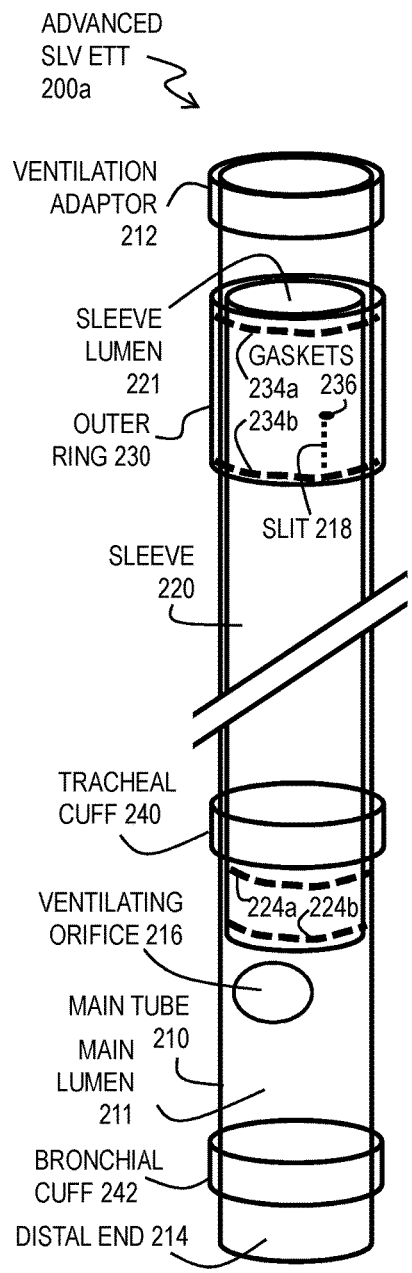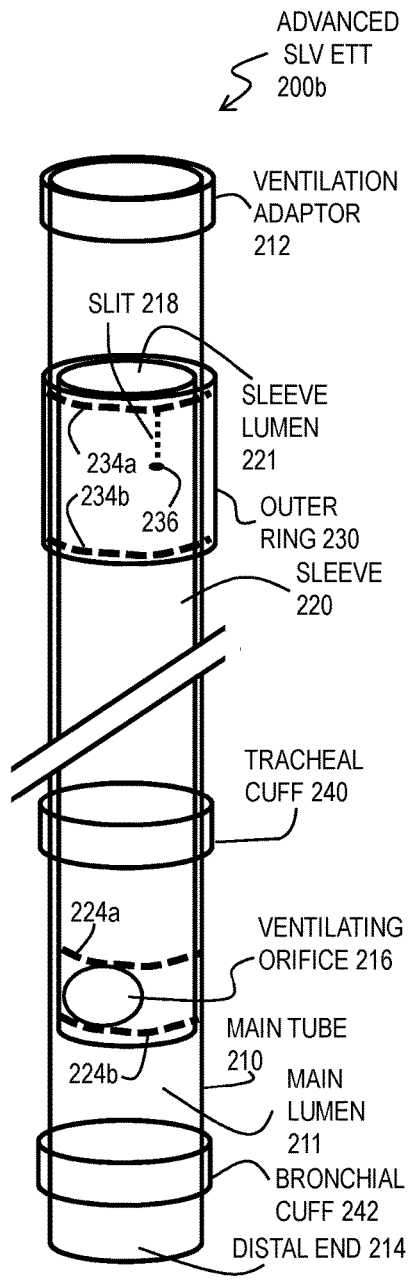

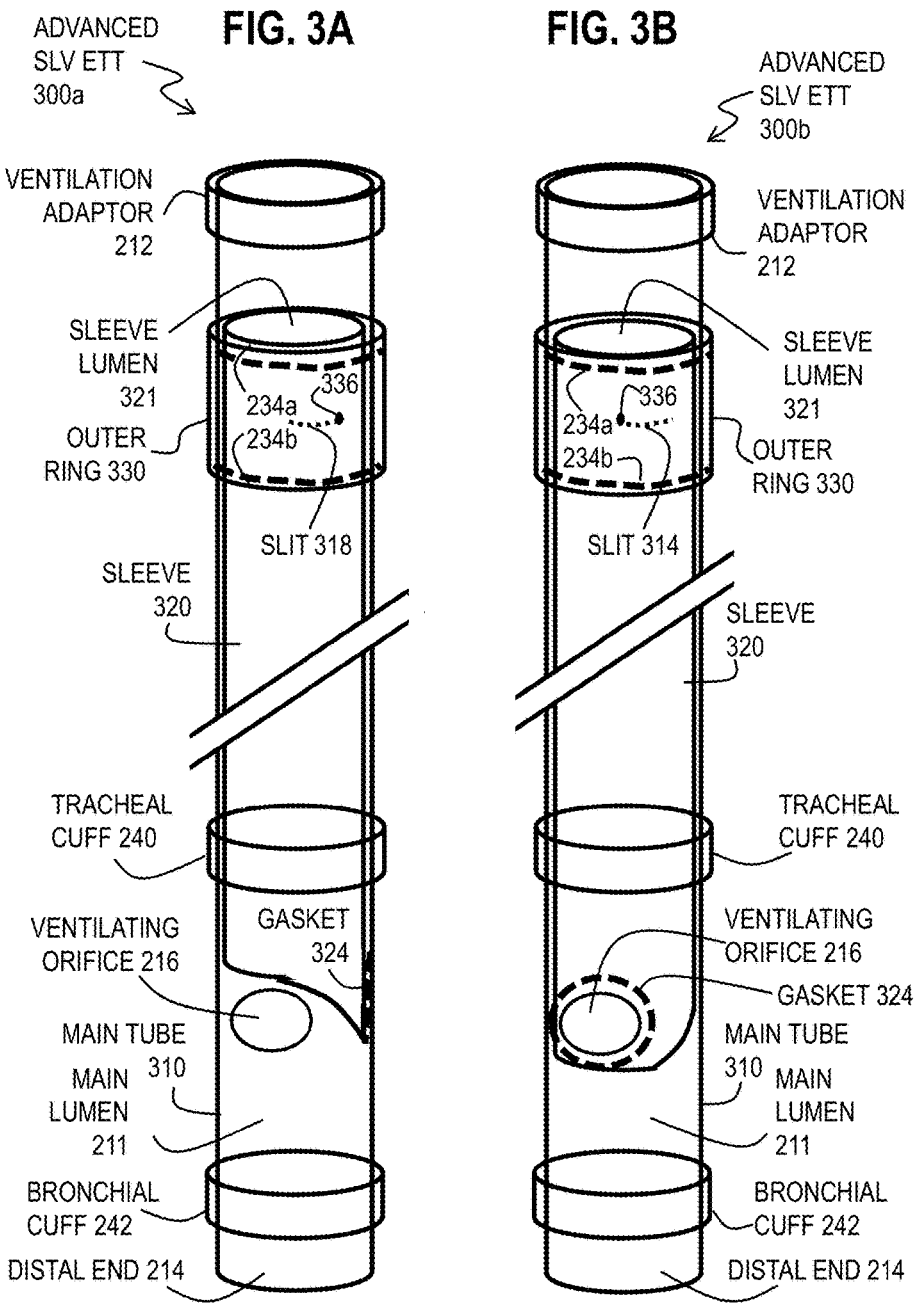

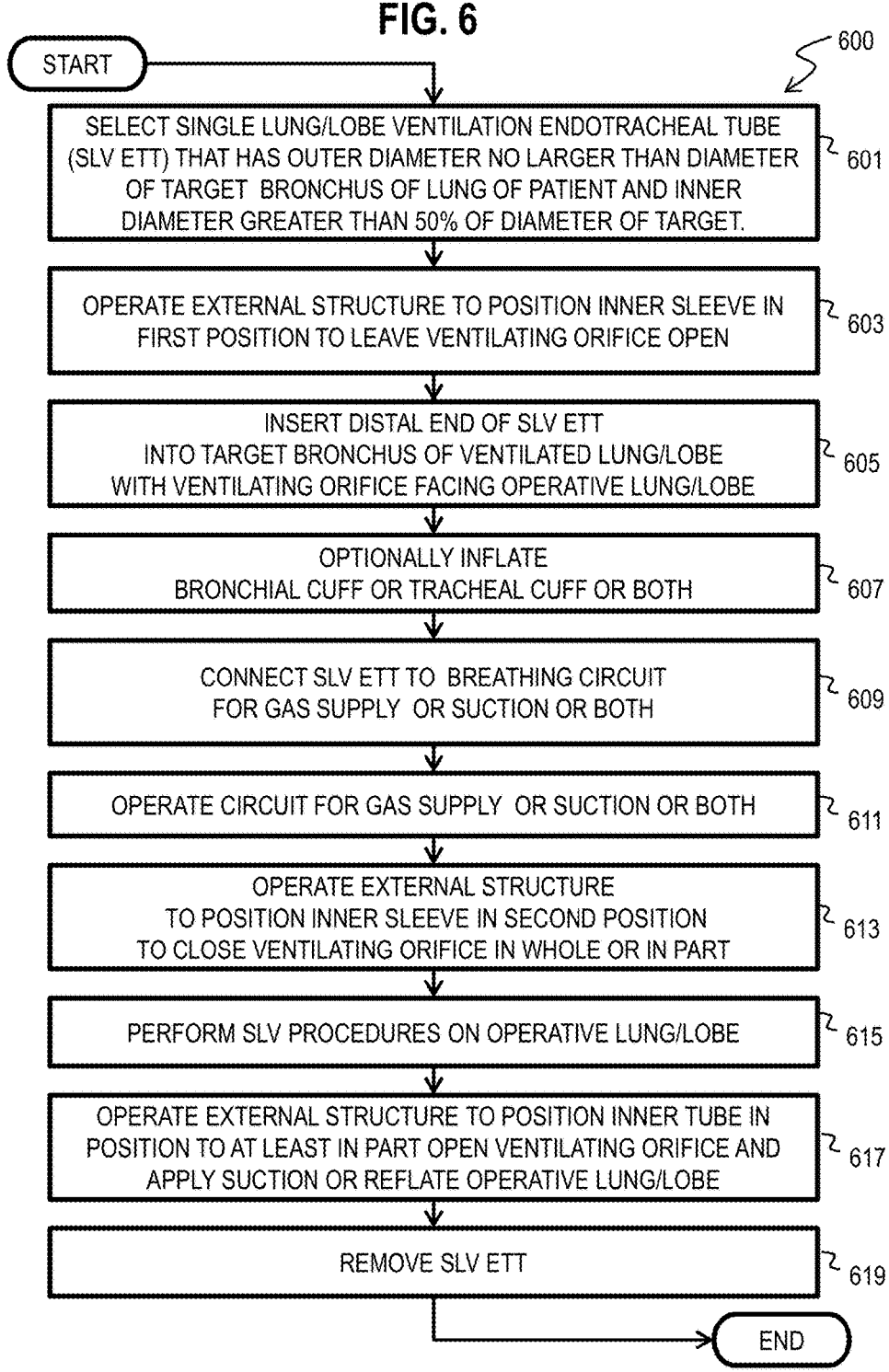

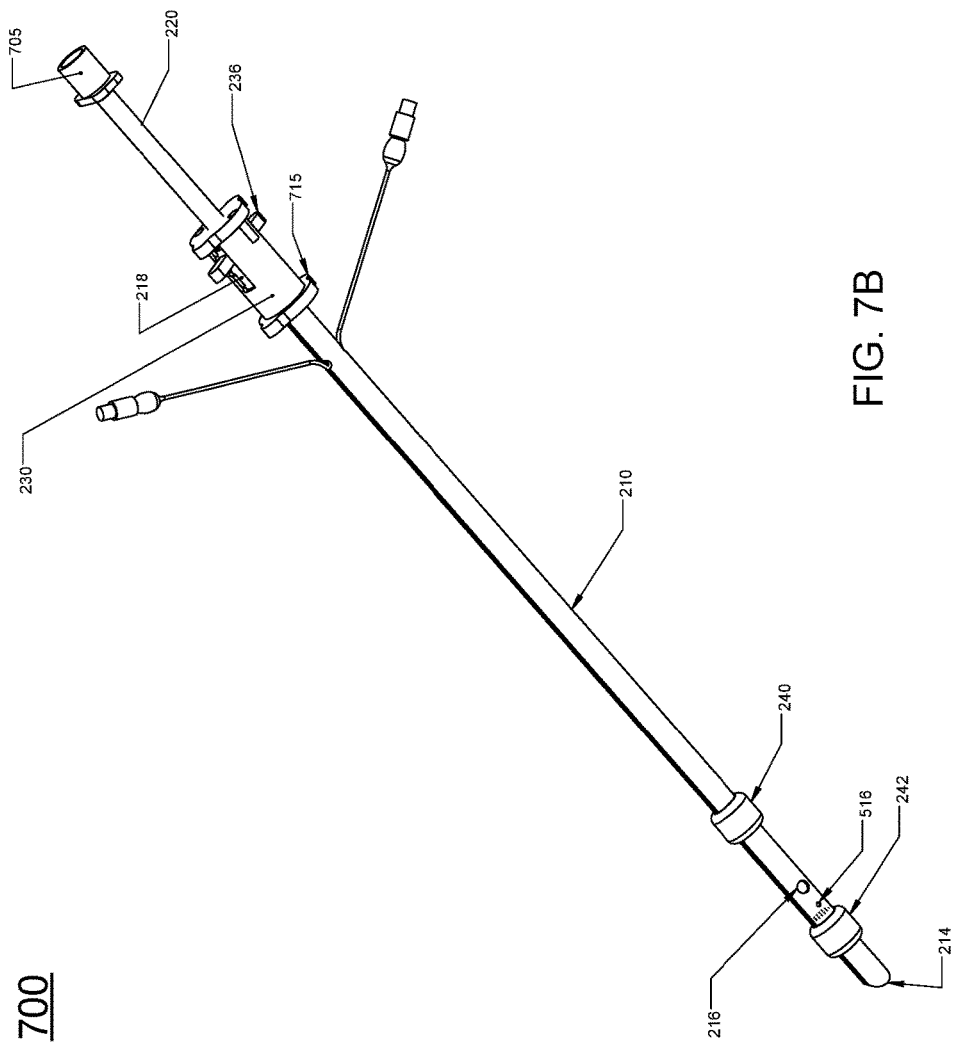

SINGLE LUNG/LOBE VENTILATION ENDOTRACHEAL TUBE

CROSS-REFERENCE TO RELATED APPLICATIONS

This application is a CONTINUATION-IN-PART of U.S. patent application Ser. No. 13/746,583 filed Jan. 22, 2013, which claims benefit of Provisional Application 61/589,335, filed Jan. 21, 2012, the entire contents of which are hereby incorporated by reference as if fully set forth herein.

BACKGROUND OF THE INVENTION

Single lung ventilation (SLV) is performed in patients undergoing thoracic surgery in order to cause deflation of the operative lung, thereby improving surgical conditions. Lung deflation allows for better visualization of structures in the chest, prevents intermittent expansion of the lung during ventilation (impairing access to intra-thoracic structures and interfering with surgical manipulation) and obviates the need for surgical retraction of the lung, which may cause trauma to the lung parenchyma. There are currently three methods of performing SLV in children: (1) placement of a conventional endotracheal tube (ETT) into the mainstem bronchus on the non-operative side (also called the side of the ventilated lung); (2) insertion of a balloon wedge catheter (bronchial blocker) into the mainstem bronchus on the operative side (also called the side of the operative lung); and (3) tracheal intubation with a double-lumen ETT (DLT). Each of these has several disadvantages.

SUMMARY OF THE INVENTION

Techniques are provided for single lung or lobe ventilation with an advanced endotracheal tube, referenced hereinafter as an advanced SLV ETT.

In a first set of embodiments, an apparatus includes a hollow main tube and a hollow tubular sleeve. The main tube has an outer diameter sized to fit inside a bronchus of a patient and a length sufficient for a distal end of the main tube to reach a first side bronchus from a proximal end configured to be located in a vicinity of a mouth of the patient. The main tube has a ventilating orifice separated from the distal end at a location that corresponds to a different second side bronchus. The sleeve is moveably disposed inside and longitudinally aligned with the main tube. The sleeve is configured to be positioned in at least two positions: a first position that does not block the ventilating orifice; and, a second position that does block the ventilating orifice.

In a second set of embodiments, a method includes selecting the above apparatus sized for a patient and causing the sleeve to be at the first position. The method also includes inserting the distal end of the main tube into the bronchus of a ventilating lobe of a lung of the patient so that the ventilating orifice faces a bronchus of a different, operative lobe of a lung of the patient. The method further includes connecting the proximal end of the main tube to a ventilation source, and moving the sleeve to the second position.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A and FIG. 2B are block diagrams that illustrate an example advanced single lung ventilation endotracheal tube (SLV ETT) in open and closed configurations, respectively, according to an embodiment;

FIG. 3A and FIG. 3B are block diagrams that illustrate an example advanced SLV ETT in open and closed configurations, respectively, according to another embodiment;

FIG. 6 is a flow chart that illustrates an example method for single lung ventilation (SLV), according to an embodiment;

FIG. 7A and FIG. 7B are block diagrams that illustrate an example advanced single lung ventilation endotracheal tube (SLV ETT) without and with an outer tube handle, respectively, according to embodiments of the invention.

DETAILED DESCRIPTION

A method and apparatus are described for single lung or lobe ventilation. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of ventilating only the left lung using inflatable cuffs so the right lung can be subject to some procedure. However, the invention is not limited to this context. In other embodiments the operative and ventilated lungs are switched, or one or more lobes of one lung are ventilated while other lobes of the same lung are subjected to some operative procedure while not-ventilated, or the main tube diameter is such that one or both of the tracheal and bronchial cuffs may be omitted, or the apparatus or use is modified in some combination of ways.

1. Overview

Figure 1A:
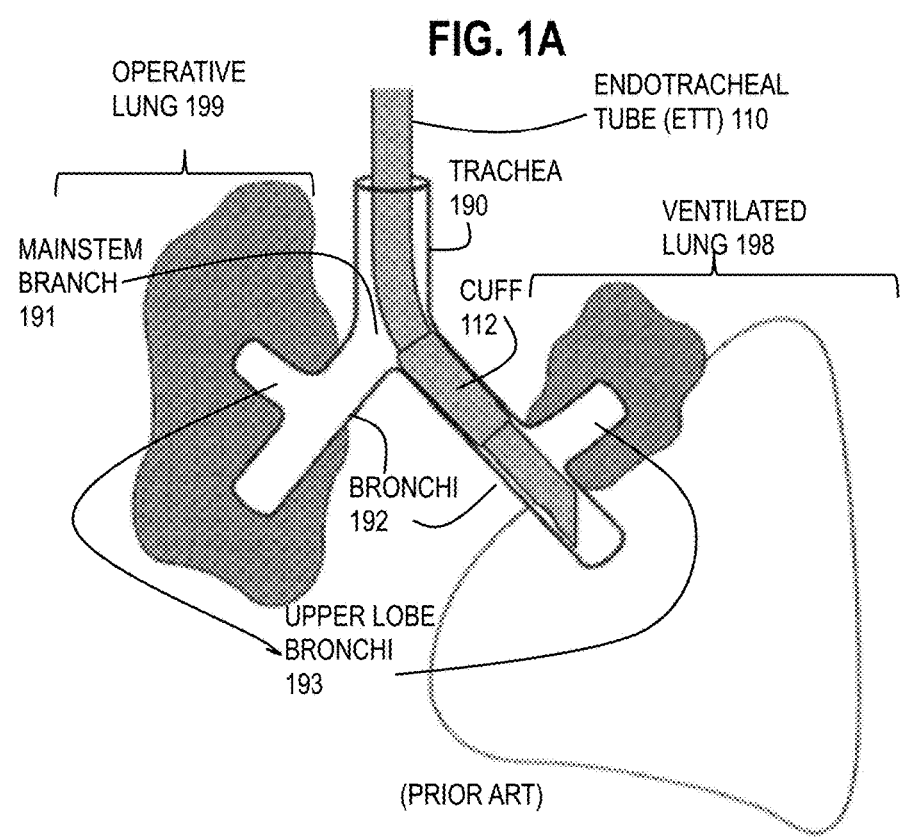
FIG. 1A is a block diagram that illustrates example use of a standard endotracheal tube for single lung ventilation (SLV)

FIG. 1A is a block diagram that illustrates example use of a standard endotracheal tube (ETT) for single lung ventilation (SLV). The endotracheal tube (ETT) 110 includes a cuff 112 and is inserted through the trachea 190 into a branch of the bronchi 192. The bronchi 192 include upper lobe bronchi 193 in each lung. Viewing the patient from the front, the patient's left lung is the ventilated lung 198 in this configuration, and the patient's right lung is the operative lung 199 that is not ventilated. The non-ventilated lung will deflate due to absorption atelectasis, as indicated by the irregular outline and dark shading.

FIG. 1A depicts one deficiency of using a standard ETT. Because the distance from the cuff 112 to the distal end of the ETT is set for ventilating both lungs at the mainstem branch of the bronchi, this distance might exceed the distance from the mainstem branch to the upper lobe bronchus 193 of the ventilated lung. This might prevent proper ventilation of the upper lobe of the ventilated lung and decrease the total ventilation delivered to the patient. Thus not only does the operative lung deflate, but the upper lobe of the ventilated lung also deflates (indicated by irregular shape and dark shading). Thus, hypoxemia may occur because of obstruction of the upper lobe bronchus.

A smaller, uncuffed ETT might not provide an adequate seal of the intubated bronchus. This may prevent the operative lung from adequately deflating. In patients with unilateral lung infection, this may fail to protect the healthy, ventilated lung from contamination by purulent material from the contralateral lung.

Whether a cuffed or uncuffed ETT is used, the operative lung cannot be suctioned with this technique.

A further disadvantage arises because use of a conventional ETT requires intraoperative repositioning of the ETT. The ETT must be un-taped, advanced into a mainstem bronchus to facilitate SLV and then re-taped; it then must be un-taped again and pulled back into the trachea to facilitate re-expansion of the deflated lung and bilateral lung ventilation. These maneuvers present the risk of inadvertent and potentially catastrophic tracheal extubation during surgery as well as increased risk of damage to the larynx and walls of the trachea and bronchi.

Figure 1B:
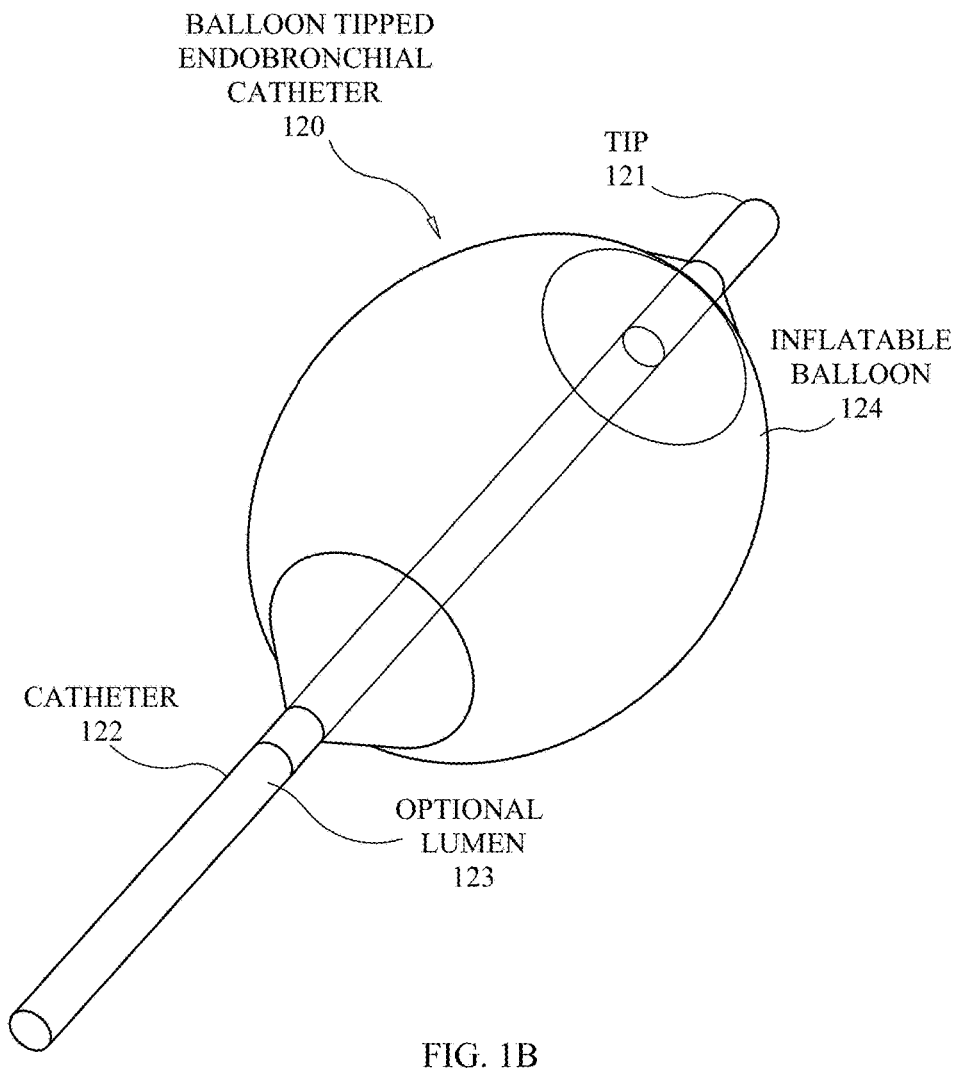
FIG. 1B is a photograph that illustrates an example balloon tipped endobronchial catheter sometimes used for single lung ventilation (SLV)

FIG. 1B is a photograph that illustrates an example balloon tipped endobronchial catheter 120 sometimes used for single lung ventilation (SLV). The device includes a catheter 122 with a tip 121 at a distal end. Near the tip 121 is an inflatable balloon 124 used to occlude a bronchus in which the tip is placed. The balloon is inflated in place by means of a tube inside the catheter 122. In some devices, the catheter 122 is hollow and the tip 121 has an opening to form an optional lumen 123.

When closed tip bronchial blockers are used with a conventional ETT; the distal end of the ETT is inserted to the mainstem branch after the balloon catheter is guided into the bronchus of the operative lung. The balloon is, then inflated to occlude the bronchus. In this configuration, the operative lung cannot be suctioned; and, oxygen and continuous positive airway pressure cannot be provided to the operative lung. Therefore, some practitioners prefer to use a bronchial blocker with an internal lumen and end-hole for SLV, as oxygen and suction may be administered via the lumen. Both types of endobronchial catheters are commonly placed outside of the ETT. Such placement requires delicate manipulation and the tracheal mucosa may be damaged by pressure exerted by the combination of the bronchial blocker and ETT. The bronchial blocker cannot be readily repositioned during surgery if it becomes dislodged.

Adapters have been used that facilitate placement of a bronchial blocker through an indwelling ETT. The risk of mucosal injury may be diminished, and repositioning of the blocker may be performed with fiber optic guidance during surgery. Problems with bronchial blocker placement through the ETT include interference with passage of a suction catheter and effective reduction of the ETT lumen (inner) diameter, compromising ventilation.

Another disadvantage with bronchial blockers is that most practitioners use fiber optic bronchoscopes to confirm the position of DLTs following placement of DLTs, whenever feasible. These instruments are expensive to purchase and their sterilization and maintenance is also costly. Alternatively, fluoroscopy may be used to confirm blocker position. The use of fluoroscopy represents significant time and expense as well as radiation exposure to the patient and operating room personnel.

Figure 1C:
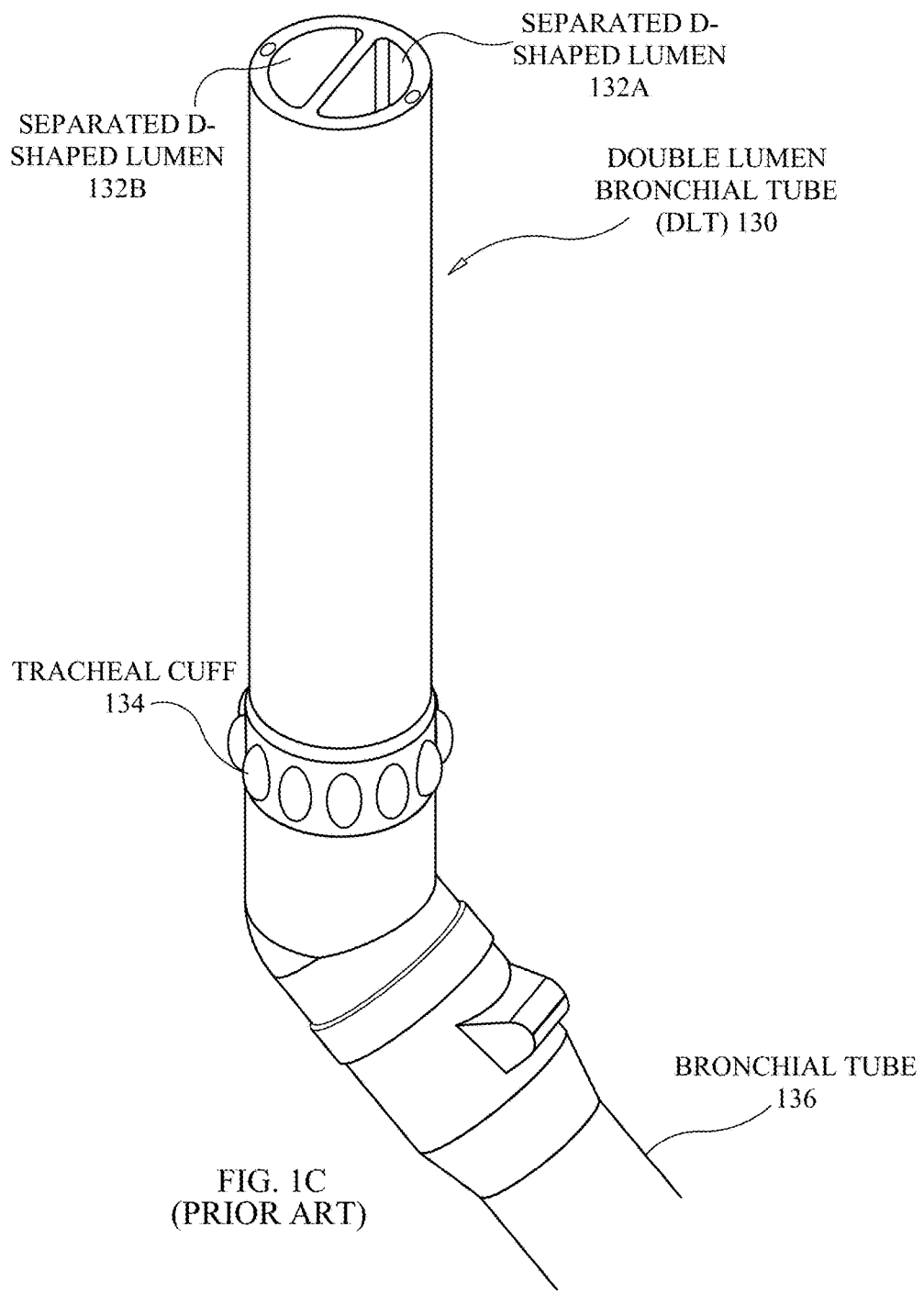
FIG. 1C is a photograph that illustrates an example double lumen bronchial tube (DLT) sometimes used for single lung ventilation (SLV)

FIG. 1C is a photograph that illustrates an example double lumen bronchial tube (DLT) 130 sometimes used for single lung ventilation (SLV). The DLT includes two separate D-shaped lumens 132a and 132b, one of which connects to a bronchial tube 136, which may include a bronchial cuff. A tracheal cuff 134 is apparent in FIG. 1C.

The use of DLTs is common in adult patients undergoing thoracic surgery. DLTs consist of a tube divided into two "D"-shaped lumens 132a and 132b. The advantages of DLT use include the ability to isolate or selectively ventilate each lung. Disadvantages include the relative stiffness and large outer diameter of these ETTs, which may present the risk of tracheal or bronchial injury. In addition, the largest round object, such as a suction catheter or fiber optic bronchoscope, that will pass down each lumen (i.e. the "working diameter") is relatively small. DLTs cannot be used in children under the age of about 10 years, as the working diameter of the lumens would be too small to allow adequate ventilation as well as passage of a suction catheter. The cost of purchase and maintenance of fiber optic bronchoscopes associated with bronchial blocker use also applies to DLTs.

The advanced SLV ETT represents a novel design for single lung or lobe ventilation that may be applied even to small children. The innovative and unique features that address the limitations of each of the three established methods for SLV include a sleeve inside a main tube and a secondary ventilating orifice in the main tube. The sleeve or inner cannula may be constructed of very thin material, thereby minimizing the functional reduction of the inner diameter of the ETT. This feature allows for optimal ventilation and passage of relatively large suction catheters compared to internally placed bronchial blockers or a DLT. As an improvement over the DLT, an inner diameter of the sleeve is greater than 50% of the outer diameter of the main tube, and preferably greater than 50% of the diameter of the target bronchus. To provide an even greater advantage, in some embodiments, the inner diameter of the sleeve is greater than about 80% of the outer diameter of the main tube or inner diameter of the bronchus. The secondary ventilating orifice is directed at the bronchus on the operative side, such as a different mainstem bronchus. When the sleeve is in a first position (e.g., "OPEN" position), the orifice is open and both lungs or lobes can be ventilated. When the sleeve is in a second position (e.g., "CLOSED" position), the orifice is occluded, the operative lung or lobe is not ventilated, and ventilation is confined to the non-operative (e.g., the "ventilated") lung or lobe or lobes.

The sleeve is disposed in the main tube. The main tube outer diameter is limited by the inner diameter of the bronchus into which it is to be inserted. Thus the main tube is made available in a variety of sizes for patients of different ages and different adult sizes, such as with an inner diameter selected from a group of diameters in a range of inner diameters from about 3.5 millimeters (mm, 1 mm=10-3 meters) to about 9 mm, such as 3.5 mm, 4.0 mm, 4.5 mm, 5.0 mm, 5.5 mm, 6.0 mm, 6.5 mm, 7.0 mm, 7.5 mm, 8.0 mm, 8.5 mm and 9.0 mm. The main tube has a length sufficient for a distal end of the main tube to reach a target bronchus in the patient from a proximal end configured to be located in a vicinity of a mouth of the patient. Thus, the main tube is available in corresponding lengths selected from a group of lengths in a range of lengths from about 22 cm (for the pediatric 3.0 mm inner diameter tube) to 34 cm (for the largest adult 9.0 mm inner diameter tube. The main tube provides the structural integrity and is constructed from any of several appropriate materials selected so that the main tube is flexible enough to follow the trachea and bronchi to the target bronchus in the patient. For example, in various embodiments, the main tube is constructed of material used in standard ETTs with similar wall thickness and inner diameters. Such materials and thicknesses include plastic (polyvinyl chloride) and other polymers with a wall thickness between 1.2 mm for the smaller (pediatric) tubes and 3.2 mm for the larger (adult) tubes. In some embodiments, the main tube or sleeve or both are tapered to be one size at the proximal end and a smaller size toward the distal end.

In some embodiments, an external structure (e.g., an outer ring) is attached to the sleeve, with which the sleeve may be moved easily between the "CLOSED" position and the "OPEN" position, to occlude or expose, respectively, the secondary ventilating orifice. In some embodiments, the external structure (e.g., the ring) is near the ETT proximal end and is readily accessible to the practitioner (e.g., an anesthetist) during surgery.

In some embodiments, an inflatable bronchial or tracheal cuff is included. The inflatable bronchial cuff or tracheal cuff is a short, low-pressure, high-volume structure. Such a cuff minimizes the likelihood of both inadvertent occlusion of a bronchus (such as the upper lobe bronchus of the ventilated lung) and also mucosal injury. In some embodiments the bronchial or tracheal cuff, or both, is not inflated but is made of a soft material that provides an effectively airtight seal. As used herein, the adjective airtight indicates substantially inhibiting the passage of any gas, including air, e.g., around the cuff at inflating pressures up to about 30 centimeters of water (cm H2O) to about 35 cm H2O.

In contrast to bronchial blockers and DLTs, placement of the SLV ETT is relatively simple. No special equipment (such as fiber optic bronchoscope or fluoroscopy) is required. Following tracheal intubation, prior to taping in place, the SLV ETT is advanced until breath sounds are lost on the operative side; it is then pulled back until breath sounds are restored and then the tube is taped at this depth. No repositioning of the ETT is required once its initial position is confirmed, in contrast to use of a conventional ETT (as described above). If oxygenation of the operative lung is desired during SLV, the sleeve may be partially moved, allowing a narrow stream of oxygen to flow to the deflated lung without causing lung expansion. Alternatively, the orifice can be opened further while a brief period of continuous positive airway pressure (CPAP) is applied; oxygenation can be restored without full inflation or ventilation of the operative lung. Again, no repositioning of the ETT itself is required during such maneuvers. Suctioning of the trachea while the sleeve is in the "OPEN" position, or partially open position, will allow evacuation of secretions and blood from the operative lung, even during surgery and lung deflation, in contrast to use of a conventional ETT.

2. Example Embodiments

FIG. 2A and FIG. 2B are block diagrams that illustrate an example advanced single lung ventilation endotracheal tube (SLV ETT) in open configuration 200a and closed configurations 200b, respectively, according to an embodiment. This embodiment of the SLV ETT itself is henceforth designated SLV ETT 200 and component elements are described in configuration 200a.

The SLV ETT 200 comprises a main tube 210 with a length sufficient for a distal end 214 of the main tube to reach a target bronchus in the patient from a proximal end configured to be located in a vicinity of a mouth of the patient. The main tube is hollow and provides a main lumen 211 to provide passage for the sleeve as well as ventilation (gas supply or effective suction), and the passage of one or more devices, such as balloon catheters through the distal end. In addition to the opening of the lumen at the distal end 214, is a secondary ventilating orifice 216. The ventilating orifice 216 is separated from the distal end 214 at a location that corresponds to a different second bronchus, when the distal end is placed into the target bronchus.

In this configuration the portion of the lung connected through the target bronchus is the ventilated lung or lobe (also called the non-operative lung or lobe). The portion of the lung connected through the different second bronchus is the operative lung or lobe (also called the non-ventilated lung or lobe). In an illustrated embodiment, the target bronchus is the left mainstem bronchus to ventilate the left lung and the second bronchus is the right mainstem bronchus to operate on the right lung. But in another embodiment, the target bronchus is the lower left lobe bronchus and the second bronchus is the upper left lobe bronchus. In some of these embodiments, another ventilating orifice is provided in the main tube to ventilate a third bronchus, such as the right mainstem bronchus, as described in more detail below with reference to FIG. 5. In various other embodiments, different ventilated lobes and operative lobes are subjected to a SLV ETT.

In the illustrated embodiment, the main tube includes a ventilation adapter 212 at the proximal end. The ventilation adaptor 212 is configured to be connected to a ventilation apparatus for providing gas at positive pressure or suction at a negative pressure. In various embodiments, any ventilating apparatus may be used with a corresponding adaptor on the proximal end of the main tube. Thus, an adaptor affixed to the proximal end of the main tube is configured for attachment to a ventilation source.

SLV ETT 200 includes a tube-shaped sleeve 220 that fits inside the main tube 210. Thus the outer diameter of sleeve 220 is less than the inner diameter of main tube 210. In the illustrated embodiment, the fit is snug enough to stay in place but loose enough to allow ready movement of the sleeve 220 relative to the tube 210. Thus, the sleeve 220 is moveably disposed inside and longitudinally aligned with the main tube 210. Because the inner sleeve 220 need not provide structural integrity, in various embodiments, the sleeve 220 is made of a thin material that can withstand physiological pressures applied to the ventilated lung or lobe. This allows the lumen 221 of the sleeve 220 to be as large as possible, for the most effective ventilation or passage of one or more other devices into the target bronchus, or some combination. The sleeve is configured to be positioned in at least two positions, a first position that does not block the ventilating orifice 216 and a second position that does block the ventilating orifice 216.

To control movement of the sleeve 220 relative to the main tube 210, a connector is provided to an external structure that can be accessed easily by an operator, such as an anesthesiologist. For example, in SLV ETT 200, a connector 236 attached to sleeve 220 passes through a slit 218 in the main tube to an outer ring 230 near the proximal end of the main tube. Thus, an external structure connected to the sleeve by a connecting element is configured to move the sleeve between the first position and the second position; and, the connecting element is moveably disposed in a slit in the main tube. In some embodiments the slit includes one or more notches that engage the connector and inhibit movement of the connector along the slit without pressure applied by an operator.

The outer ring is configured to be airtight, e.g., to prevent significant leakage of gas between the main lumen 211 and the ambient air. In some embodiments, the length of the ring 230 is selected so that sufficient contact between ring 230 and main tube 210 prevents significant exchange of gas. In the illustrated embodiment, the interior of ring 230 or exterior of main tube 210 is configured with one or more gaskets (such as gasket 234a and gasket 234b, collectively referenced hereinafter as gaskets 234) to allow no, or only negligible, exchange of gas between the main lumen 211 and the ambient air. In some embodiments, the ring 230 is omitted and the slit 218 includes an airtight gasket through which the connector 236 can be moved by operator contact with an external projection or handle of the connector 236.

In some embodiments, the SLV ETT includes a bronchial cuff 242 or tracheal cuff 240 or both. The cuffs are configured to block the exchange of gas outside the main tube 210, especially when the bronchus or trachea, or both, has a larger inner diameter than the outer diameter of the main tube between the distal end of the main tube emplaced in the patient's target bronchus and the patient's mouth. The cuffs 240 and 242 are made of any pliable material that can conform to the inner surface of the trachea or bronchus, respectively, and inhibit the flow of gas. For example, the same material currently used in a cuff for a conventional ETT or DLT is used in some embodiments. In some embodiments, the cuffs 240 or 242 or both are balloons cuffs that can be inflated to conform to the inner surface of the trachea or bronchus, respectively, and inhibit the flow of gas. In some embodiments, each balloon cuff is fed by a thin tube that runs along the outer edge of the main tube 210 and diverges near the proximal end of the main tube to connect to a pilot balloon (not shown).

In some embodiments, the bronchial cuff 242 is displaced from the distal end 214 of the main tube to a location that corresponds to a location between the target bronchus and the second bronchus. Thus, the bronchial cuff 242 is disposed on the main tube 210 between the distal end 214 and the ventilating orifice 216. In some embodiments, the tracheal cuff 240 is displaced from the distal end 214 of the main tube to a location that corresponds to a location between the second bronchus and the next larger bronchus, such as the trachea. Thus, the tracheal cuff 240 is disposed on the main tube between the proximal end and the ventilating orifice 216.

In some embodiments, the sleeve 220 in the second position blocks the ventilating orifice 216 with an airtight seal. In the illustrated embodiment, the sleeve includes one or more gaskets, such as gasket 224a and gasket 224b (collectively referenced hereinafter as gaskets 224) to provide an airtight seal when the sleeve is in the second position. Any suitable material may be used for gaskets 224, such as rubber. Thus, the sleeve is configured to form an airtight seal at ventilating pressures with the main tube surrounding the ventilating orifice when the sleeve is in the second position.

FIG. 2A depicts SLV ETT 200a configured in a first position in which the ventilating orifice 216 is not blocked by the sleeve 220. FIG. 2B depicts SLV ETT 200b configured in a second position in which the ventilating orifice 216 is blocked by the sleeve 220. All components in FIG. 2B are already described above with reference to FIG. 2A. When the sleeve is moved to the second position, e.g., by an operator moving ring 230 downward toward the distal end 214, the orifice 216 is blocked by the sleeve 220. The gaskets 224 ensure an airtight seal. Thus, the sleeve is displaced longitudinally toward the distal end in the second position compared to the first position. In some embodiments, the sleeve 220 or connector 236 or slit 218 is configured so the sleeve 220 can be stopped in one or more positions between the first position and the second position so as to block the ventilating orifice 216 only partially. Thus, in such embodiments, the sleeve is further configured to be positioned in a third position that partially blocks the ventilating orifice.

Figure 2C:
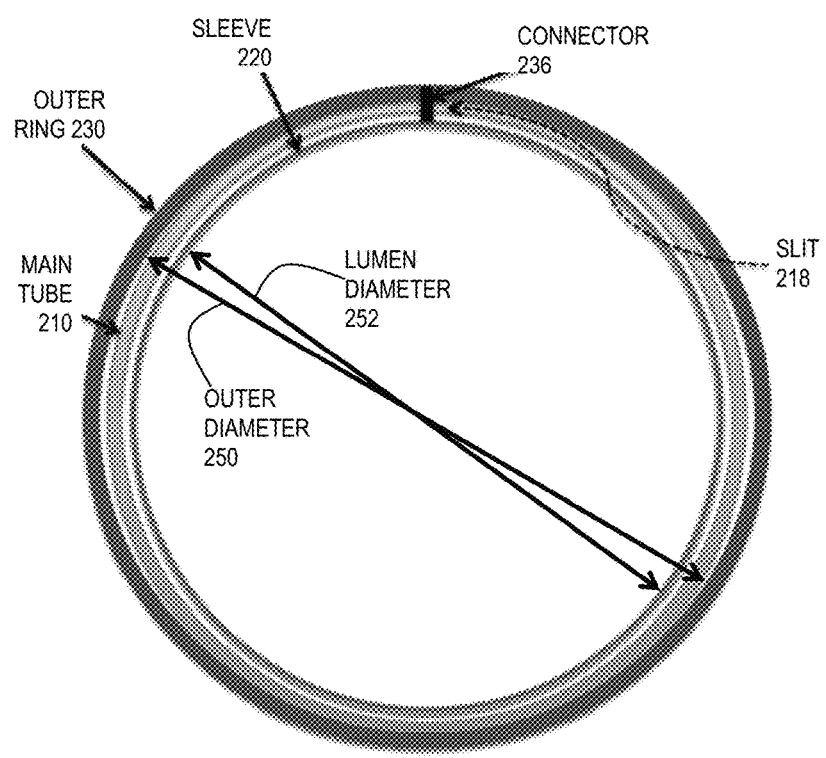
FIG. 2C is a block diagram that illustrates an example cross section near the proximal end of the SLV ETT of FIG. 2A and FIG. 2B, according to an embodiment.

FIG. 2C is a block diagram that illustrates an example cross section near the proximal end of the SLV ETT 200 of FIG. 2A and FIG. 2B, according to an embodiment. The inner sleeve 220 fits inside the main tube 210. A connector 236 connects the sleeve 220 to the outer ring 230 through the longitudinal slit 218 in the main tube 210. The sleeve lumen diameter 252, which is the inner diameter of sleeve 220, is smaller than the main tube outer diameter 250, but the sleeve lumen diameter 252 is much greater than 50% of that diameter 250. In the illustrated embodiment, the sleeve lumen diameter 252 is about 80% of the main tube outer diameter. Thus, when the main tube is snug in the trachea or bronchus, the sleeve lumen is about 80% of the natural lumen, providing improved ventilation (including gas supply and suction) and access.

FIG. 3A and FIG. 3B are block diagrams that illustrate an example advanced SLV ETT in open configuration 300a and closed configuration 300b , respectively, according to another embodiment. This embodiment of the SLV ETT itself is henceforth designated SLV ETT 300 and component elements are described in configuration 300a. Ventilator adaptor 212, gasket 234a, gasket 234b, tracheal cuff 240, ventilating orifice 216, main lumen 211, bronchial cuff 242 and distal end 214 are as described above with reference to FIG. 2A. Main tube 310 includes an azimuthal slit 318 in place of the longitudinal slit 218 of SLV ETT 200. Connector 336 is configured to move through azimuthal slit 318 and outer ring 330 is configured to be rotated relative to the main tube 310 rather than moved longitudinally. Sleeve 320 has an azimuthally dependent length and a differently configured gasket 324 to provide for airtight blockage of ventilating orifice 216.

FIG. 3A depicts SLV ETT 300a configured in a first position in which the ventilating orifice 216 is not blocked by the sleeve 320. FIG. 3B depicts SLV ETT 300b configured in a second position in which the ventilating orifice 216 is blocked by the sleeve 320. All components in FIG. 3B are already described above with reference to FIG. 3A. When the sleeve is moved to the second position, e.g., by an operator rotating ring 330 azimuthally, the orifice 216 is blocked by the sleeve 320. The gasket 324 ensures an airtight seal. Thus, the sleeve is rotated in the second position compared to the first position. In some embodiments, the sleeve 320 or connector 336 or slit 318 is configured so the sleeve 320 can be stopped in one or more positions between the first position and the second position so as to block the ventilating orifice 216 only partially. Thus, the sleeve is further configured to be positioned in a third position that partially blocks the ventilating orifice.

In other embodiments other movements of the sleeve are utilized. For example in some embodiments, the slit is aligned with both longitudinal and azimuthal displacements; and, the ring is both rotated and moved longitudinally to move between the first position and the second position.

Figure 3C:
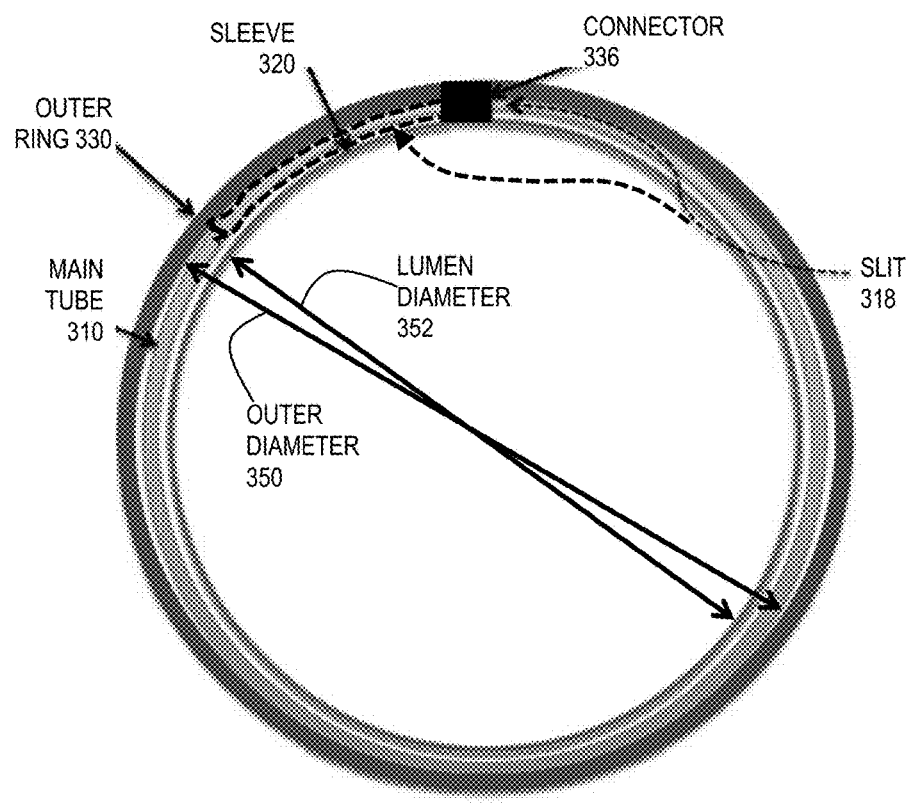
FIG. 3C is a block diagram that illustrates an example cross section near the proximal end of the SLV ETT of FIG. 3A and FIG. 3B, according to this embodiment.

FIG. 3C is a block diagram that illustrates an example cross section near the proximal end of the SLV ETT 300 of FIG. 3A and FIG. 3B, according to this embodiment. The inner sleeve 320 again fits inside the main tube 310. A connector 336 connects the sleeve 320 to the outer ring 330 through the azimuthal slit 318 in the main tube 310. The sleeve lumen diameter 352, which is the inner diameter of sleeve 320, is smaller than the main tube outer diameter 350, but the sleeve lumen diameter 352 is much greater than 50% of that diameter 350. In the illustrated embodiment, the sleeve lumen diameter 352 is about 80% of the main tube outer diameter 350. Thus, when the main tube is snug in the trachea or bronchus, the sleeve lumen is still about 80% of the natural lumen, again providing improved ventilation (including gas supply and suction) and access, compared to other devices used for SLV.

Figure 4A:
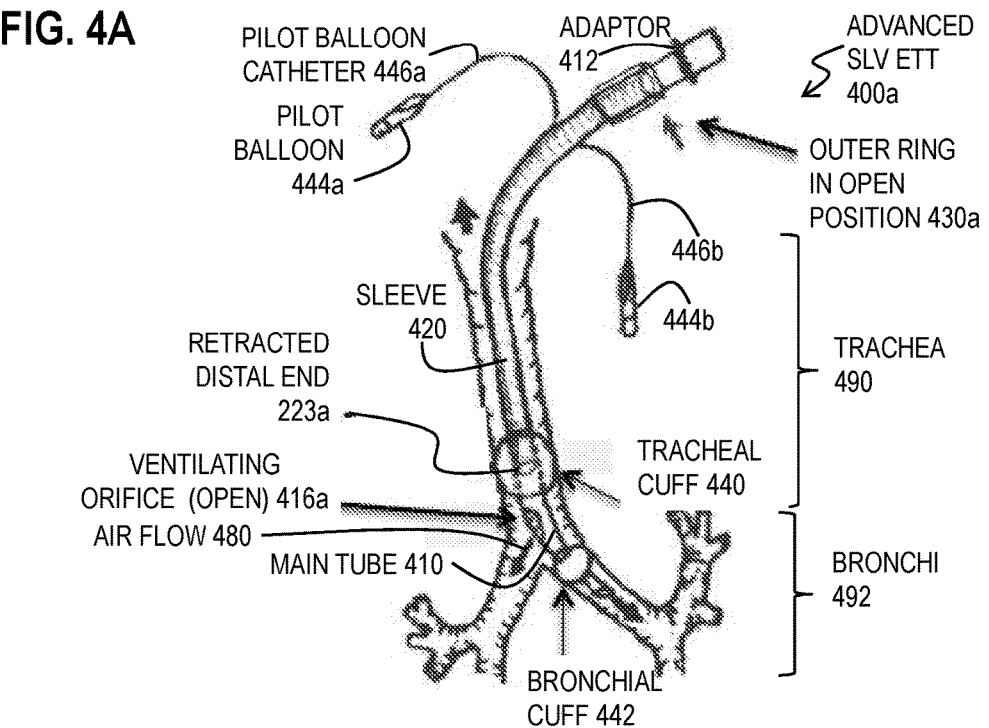
FIG. 4A and FIG. 4B are block diagrams that illustrate an SLV ETT deployed in a patient in open and closed configurations, respectively, according to an embodiment.
Figure 4B:
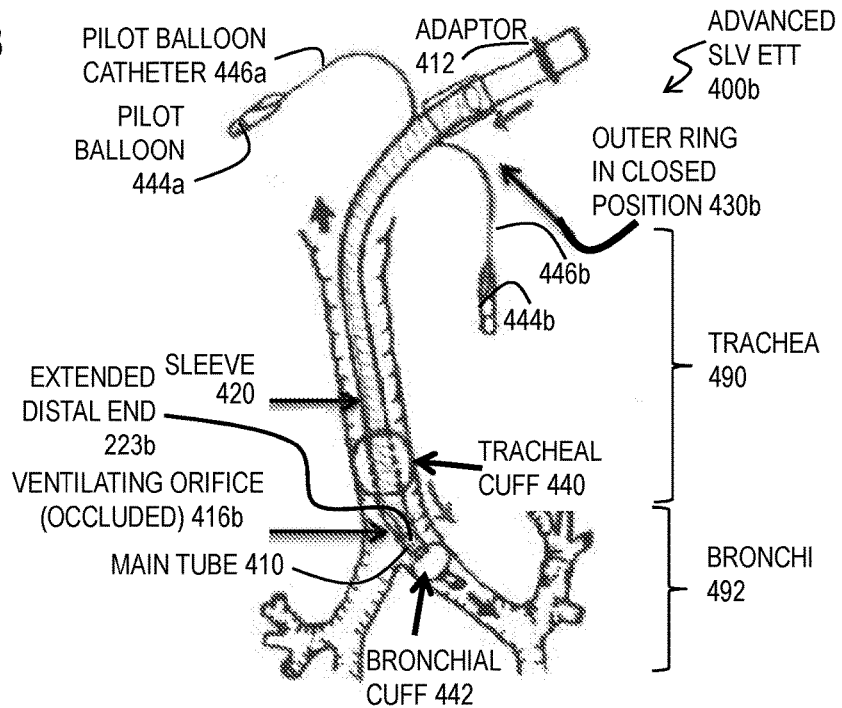

FIG. 4A and FIG. 4B are block diagrams that illustrate an SLV ETT deployed in a patient in open configuration 400a and closed configuration 400b, respectively, according to an embodiment. This embodiment of the SLV ETT itself is henceforth designated advanced SLV ETT 400 and component elements are described in configuration 400a. SLV ETT 400 is similar to SLV ETT 200 with longitudinally moving sleeve 220; but, SLV ETT includes inflatable tracheal cuff 440 and inflatable bronchial cuff 442, with corresponding pilot balloons 444a, 444b and catheters 446a, 446b, respectively, used with inflatable cuffs. The main tube 410 with ventilating orifice 416 is depicted along with ventilation adaptor 412, and sleeve 420. The distal end of main tube 410 and bronchial cuff 442 are disposed in the left mainstem bronchus of the bronchi 492 of the patient. The tracheal cuff 440 is disposed in the trachea 490 of the patient. The ventilating orifice 416 is facing the patient's right mainstem bronchus.

In FIG. 4A, the outer ring is in open position 430a, the sleeve 420 has a retracted distal end 223a, the ventilating orifice is not blocked, and gas or air flow 480 is freely directed into the right mainstem bronchus as well as through the distal end of the main tube 410 into the patient's left mainstem bronchus. In FIG. 4B, the outer ring is in closed position 430b, the sleeve 420 has a longitudinally extended distal end 223b, the ventilating orifice 416 is blocked, and gas or air flow into the right mainstem bronchus is absent, while air flows freely into the left mainstem bronchus. The patient's right lung (on viewer's left) will deflate as is suitable for certain operations on the patient's right lung, while the patient's left lung remains ventilated.

Figure 5:
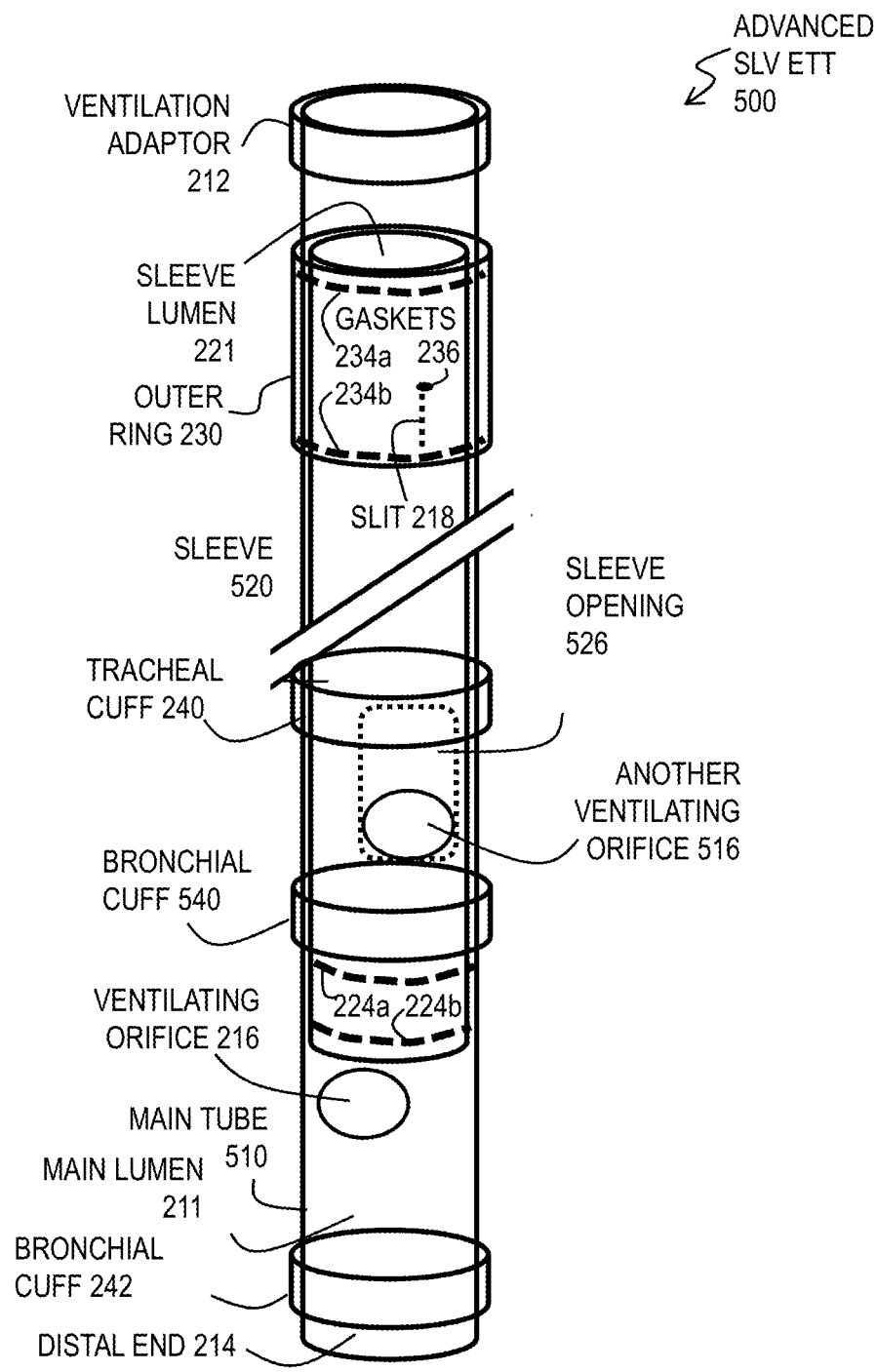
FIG. 5 is a block diagram that illustrates an single lobe ventilation ETT, according to yet another embodiment.

FIG. 5 is a block diagram that illustrates a SLV ETT 500 for operating on a single lobe, according to yet another embodiment. This SLV ETT 500 ventilates lobes both upstream and downstream of the operative lobe. The SLV ETT 500 includes a ventilation adaptor 212, main lumen 211, distal end 214, slit 218, ring 230, connector 236, gasket 234a, gasket 234b, gasket 224a, gasket 224b, ventilating orifice 216, sleeve lumen 221, tracheal cuff 240 and bronchial cuff 242 as described above with reference to FIG. 2A. However, this embodiment includes a main tube 510 with another ventilating orifice 516 to ventilate a bronchus upstream of the operative lobe. To keep this orifice open even when the orifice 216 is blocked, tubular inner sleeve 520 includes a sleeve opening 526 that prevents blockage of the orifice 516 when the sleeve is moved longitudinally. The second cuff is a second bronchial cuff 540 configured for positioning inside a bronchus instead of the trachea. This embodiment provides the advantage of isolating the operative lobe from upstream lobes.

In the open configuration depicted, gas, such as air, flows freely through the main lumen 211 at the distal end 214 of the main tube 510 as well as through the ventilating orifice 216 and the other ventilating orifice 516. In the closed configuration, the sleeve 520 blocks ventilating orifice 216, with gaskets 224 and 224b providing an airtight seal. However, air flows freely through the distal end 214 and the other ventilating orifice 516. Referring to FIG. 1A, the SLV ETT 500, when in the closed configuration, is capable of ventilating the patient's entire right lung through the other ventilating orifice 516 and the lower lobe of patient's left lung through the distal end 214 of the main tube, while not ventilating the upper lobe of the patient's left lung. Thus, a surgical procedure can be performed in the vicinity of the upper lobe of the patient's left lung.

Figure 7A:
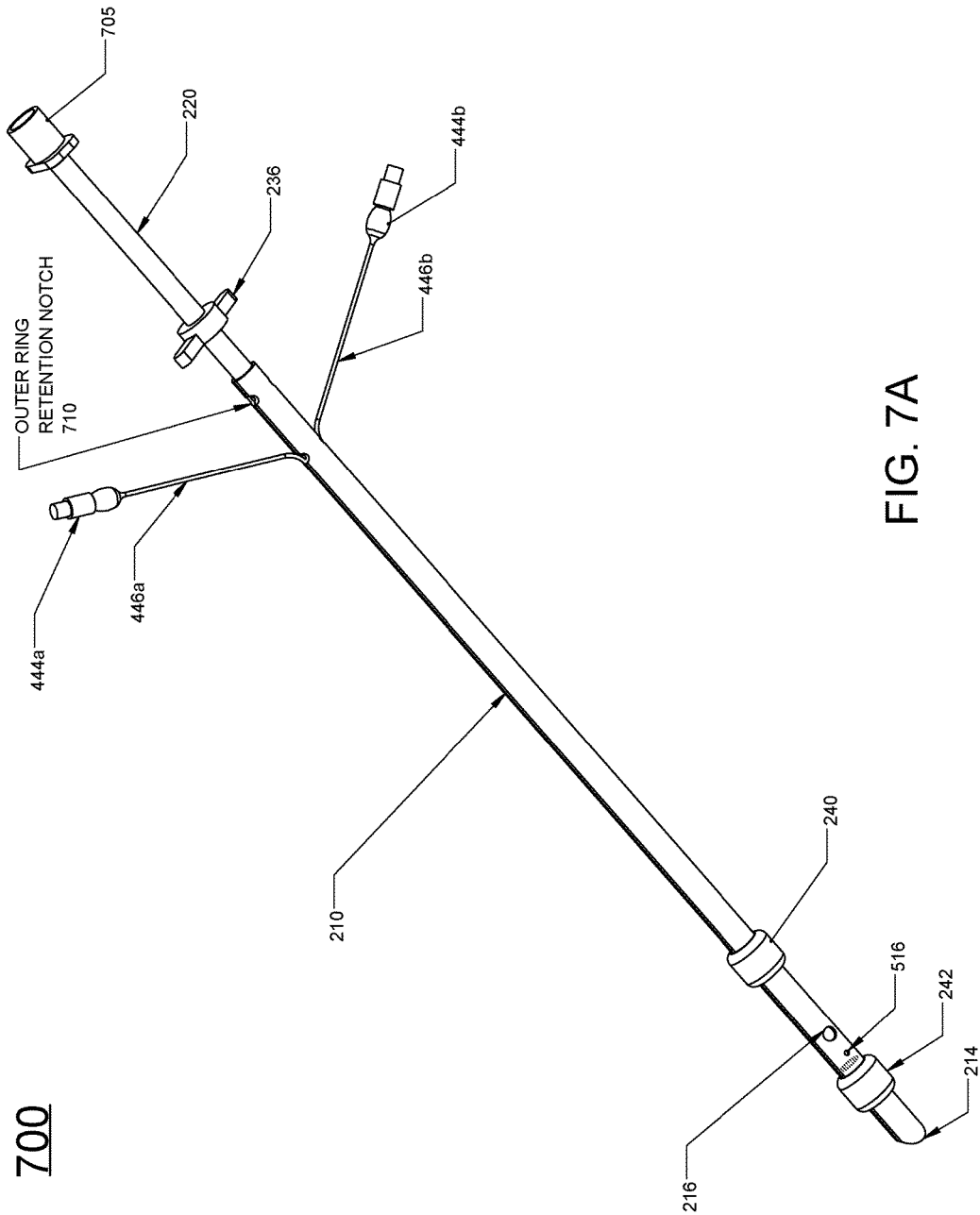
Figure 7C:
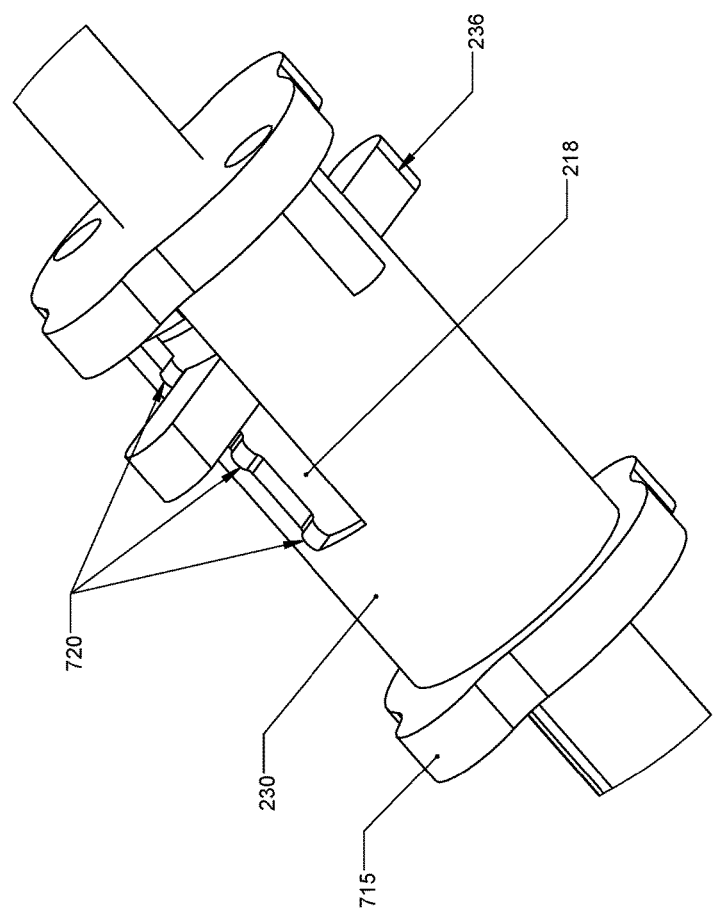
FIG. 7C is a block diagram that illustrates a close up view of the a portion of the SLV ETT, according to embodiments of the invention.

FIG. 7A and FIG. 7B are block diagrams that illustrate an exemplary advanced single lung ventilation endotracheal tube (SLV ETT) 700 without and with an outer ring/outer tube handle, respectively. FIG. 7C is a block diagram that illustrates a close up view of the outer ring 230 and portions of the SLV ETT 700 proximate to outer ring 230 shown in FIGS. 7A and 7B.

The SLV ETT 700 comprises a main tube 210 with distal end 214, second ventilating orifice 216, pilot balloons 444a and 444b, pilot balloon catheters 446a and 446b, an outer ring retention notch 710, a main tube handle 715, outer ring 230, sleeve 220, slits 218, connector 236, and an adaptor 705. The main tube 210 may have a length sufficient for a distal end 214 of the main tube 210 to reach a target bronchus in the patient from a proximal end configured to be located in a vicinity of a mouth of the patient.

The main tube 210 is hollow and provides a lumen that allows for passage for the sleeve 220 as well as ventilation (gas supply or effective suction) and the passage of one or more devices, such as balloon catheters through the distal end 214. In some embodiments, the sleeve 220 may be sized and positioned within the lumen of main tube 210 so that air, or other gases, cannot pass between sleeve 220 and main tube 210. Additionally, or alternatively, a lubricant or coating (e.g., a hydrophobic coating) may be applied to an exterior surface of sleeve 220, an interior surface of main tube 210, or both so as to, for example, facilitate sliding, or otherwise moving, sleeve 220 relative to main tube 210. In addition to the opening of the lumen at distal end 214 (which provides a first, or primary, ventilating orifice), main tube 210 may also include a second, or secondary, ventilating orifice 216 and an optional third ventilating orifice 516, (also referred to herein as "another ventilating orifice 516") both of which may be positioned near the distal end 214. The third ventilating orifice 516 may be used to ventilate a bronchus upstream of the operative lobe. To keep this third ventilating orifice 516 open even when the secondary orifice 216 is blocked, sleeve 220 may include a sleeve opening (not shown) that prevents blockage of the third ventilating orifice 516 when the sleeve 220 is moved longitudinally.

This embodiment provides the advantage of isolating the operative lobe from upstream lobes.

When SLV ETT 700 includes a third ventilating orifice 516, gas, such as air, may flow freely through the lumen of main tube 210 at the distal end 214 of the main tube 210 as well as through the secondary ventilating orifice 216 and the third ventilating orifice 516. In the closed configuration, the sleeve 220 may block the second ventilating orifice 216 and provide an airtight seal. However, air may flow freely through the distal end 214 and the third ventilating orifice 516. Referring to FIG. 1A, the SLV ETT 700, when in the closed configuration, is capable of ventilating the patient's entire right lung through the third ventilating orifice 516 and the lower lobe of patient's left lung through the distal end 214 of the main tube, while not ventilating the upper lobe of the patient's left lung. Thus, a surgical procedure can be performed in the vicinity of the upper lobe of the patient's left lung.

In this configuration the portion of the lung connected through the target bronchus is the ventilated lung or lobe (also called the non-operative lung or lobe). The portion of the lung connected through the different second bronchus is the operative lung or lobe (also called the non-ventilated lung or lobe). In an embodiment, the target bronchus is the left mainstem bronchus to ventilate the left lung and the second bronchus is the right mainstem bronchus to operate on the right lung. But in another embodiment, the target bronchus is the lower left lobe bronchus and the second bronchus is the upper left lobe bronchus. In some of these embodiments, another ventilating orifice (not shown) is provided in the main tube to ventilate a third bronchus, such as the right mainstem bronchus, as described in more detail above with reference to FIG. 5. In various other embodiments, different ventilated lobes and operative lobes are subjected to a SLV ETT like SLV ETT 700.

SLV ETT 700 includes a tube-shaped sleeve 220 that fits inside the main tube 210. Thus the outer diameter of sleeve 220 is less than the inner diameter of main tube 210. In the illustrated embodiment, the fit is snug enough to stay in place but loose enough to allow ready movement of the sleeve 220 relative to the tube 210. Thus, the sleeve 220 is moveably disposed inside, and longitudinally aligned with, the main tube 210. Because the inner sleeve 220 need not provide structural integrity, in various embodiments, the sleeve 220 is made of a thin material that can withstand physiological pressures applied to the ventilated lung or lobe. This allows the lumen of the sleeve 220 to be as large as possible, for the most effective ventilation or passage of one or more other devices into the target bronchus, or some combination. The sleeve 220 is configured to be positioned in at least two positions, a first position that does not block the ventilating orifice 216 and a second position that does block the ventilating orifice 216. Outer ring 230 may be configured to facilitate movement of the sleeve 220 relative to the main tube 210, as well as enable handling of SLV ETT 700.

SLV ETT 700 may include a ventilation adaptor 705 coupled to sleeve 220. The ventilation adaptor 705 is configured to connect to a ventilation apparatus for providing gas at positive pressure or suction at a negative pressure. In various embodiments, any ventilating apparatus may be used with a corresponding adaptor on the proximal end of the sleeve 220. Thus, the ventilation adaptor 705 affixed to the proximal end of the sleeve 220 is configured for attachment to a ventilation source.

Sleeve 220 may also include connector 236 affixed thereto. The connector 236 provided by FIGS. 7A, 7B, and 7C has two extensions that are configured to be positioned within two slits 218, which are positioned on either side of outer ring 230 (only one slit 218 is shown in FIGS. 7B and 7C). In this way, the extensions of the connector 236 protrude through slits 218 so that sleeve 220 may be moved from a first position to a second position and/or from a second position to a third position (and vise versa) when pressure is applied to the connector 236 and/or extensions of the connector 236 by an operator, such as an anesthesiologist. In some circumstances, the operator may hold main tube handle 715 still and apply pressure to connector 236 and/or connector extensions to move the sleeve 220 from a first position to a second position and/or from a second position to a third position (and vise versa).

In some embodiments, slits 218 include one or more notches 720 that engage the connector 236 and/or extensions of the connector 236 and inhibit movement of the connector 236 along the slits 218 without pressure applied by the operator. For example, slits 218 may include 3 notches 720, which may correspond to a first, second, and third position of sleeve 220 when the connector 236 and/or the connector extensions are positioned therein. In this example, when sleeve 220 is in a first position, second ventilating orifice 216 may be open (i.e., sleeve 220 does not occlude second ventilating orifice 216). When sleeve is in a second position (which corresponds to the second, or middle, notch 720), second ventilating orifice 216 may be partially occluded by sleeve 220. When sleeve is in a third position (which corresponds to the third notch 720, or the notch closest to distal end 214), second ventilating orifice 216 may be fully occluded by sleeve 220. In some instances, the third position of sleeve 220 of this embodiment may correspond to the second position of sleeve 220 as discussed elsewhere herein, in that when sleeve 220 is in the third position, second ventilating orifice 216 is completely occluded.

In some embodiments, the sleeve 220 in the second position blocks the ventilating orifice 216 with an airtight seal. In some embodiments, the sleeve 220 includes one more gaskets, to provide an airtight seal when the sleeve 220 is in the first and/or second position. Any suitable material may be used for gaskets, such as rubber or plastic. Thus, the sleeve is configured to form an airtight seal at ventilating pressures with the main tube surrounding the ventilating orifice when the sleeve is in the second position.

In some embodiments, the bronchial cuff 242 is displaced from the distal end 214 of the main tube to a location that corresponds to a location between the target bronchus and the second bronchus. Thus, the bronchial cuff 242 is disposed on the main tube 210 between the distal end 214 and the ventilating orifice 216. In some embodiments, the tracheal cuff 240 is displaced from the distal end 214 of the main tube to a location that corresponds to a location between the second bronchus and the next larger bronchus, such as the trachea. Thus, the tracheal cuff 240 is disposed on the main tube between the proximal end and the ventilating orifice 216.

Although slits 218 are oriented in a direction substantially parallel with that of the main tube 210 and the sleeve 220, this is not necessarily the case. For example, slits 218 may be oriented perpendicularly or at an angle relative to main tube 210 and the sleeve 220.

The main tube 210 may include the main tube handle 715, which may be configured to enable the operator to handle SLV ETT 700. In some embodiments, the operator may use main tube handle 715 to stabilize SLV ETT 700 within a patient while applying pressure to connector 236 and/or extensions of the connector 236 so as to move the sleeve 220 from the first position to the second position (and vise versa).

In the illustrated embodiment, the sleeve 220 includes a ventilation adapter 705 at the proximal end. The ventilation adaptor 705 is configured to be connected to a ventilation apparatus for providing gas at positive pressure or suction at a negative pressure. In various embodiments, any ventilating apparatus may be used with a corresponding adaptor 705 on the proximal end of the sleeve 220. Thus, the ventilation adaptor 705 affixed to the proximal end of the sleeve 220 is configured for attachment to a ventilation source.

In some embodiments, the SLV ETT 700 includes a bronchial cuff 242 or tracheal cuff 240 or both. The cuffs 242 and 240 are configured to block the exchange of gas outside the main tube 210, especially when the bronchus or trachea, or both, has a larger inner diameter than the outer diameter of the main tube between the distal end of the main tube emplaced in the patient's target bronchus and the patient's mouth. The cuffs 240 and 242 are made of any pliable material that can conform to the inner surface of the trachea or bronchus, respectively, and inhibit the flow of gas. For example, the same material currently used in a cuff for a conventional ETT or DLT may be used in some embodiments. In some embodiments, the cuffs 240 or 242, or both, are balloon cuffs that can be inflated to conform to the inner surface of the trachea or bronchus, respectively, and inhibit the flow of gas. In some embodiments, each balloon cuff may be fed by a thin tube that runs along an outer or inner edge of the main tube 210 and diverges near the proximal end of the main tube to connect to a pilot catheter 446a, 446b and a pilot balloon 444a, 444b.

3. Method

FIG. 6 is a flow chart that illustrates an example method 600 for single lung or lobe ventilation (SLV), according to an embodiment. Although steps are depicted in FIG. 6 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 601, an advanced single lung/lobe endotracheal tube (SLV ETT) is selected among a plurality of SLV ETT sizes available. The selection is made so that an outer diameter of the distal end of the SLV ETT is no larger than the inner diameter of a target bronchus of a lung of a patient and an inner diameter of the SLV ETT is greater than 50% of the inner diameter of the target bronchus. For example, an advanced SLV ETT is selected that has an outer diameter in a range from about 3.5 mm to about 9 mm. The advanced SLV ETT includes a hollow main tube with outer diameter sized to fit inside a bronchus of a patient and a length sufficient for a distal end of the main tube to reach a first side (e.g., target) bronchus from a proximal end configured to be located in a vicinity of a mouth of the patient. The hollow main tube has a ventilating orifice separated from the distal end at a location that corresponds to a different second side bronchus. The advanced SLV ETT also has a hollow tubular sleeve moveably disposed inside and longitudinally aligned with the main tube, wherein the sleeve is configured to be positioned in at least two positions, a first position that does not block the ventilating orifice and a second position that does block the ventilating orifice In step 603, the sleeve is caused to be at the first position. For example, an external structure, such as a ring near the proximal end of the main tube, connected to the inner sleeve of the SLV ETT is operated to position the inner sleeve in the first position to leave open the ventilating orifice, e.g., by pulling the ring 230 toward the proximal end or by rotating the ring 330 to avoid blocking the ventilating orifice 216. If the sleeve is already in the open position, then nothing is operated to cause the sleeve to be in the open position during step 603.

In step 605, the distal end of the advanced SLV ETT is inserted into a target bronchus of a ventilated lung or lobe thereof, with the ventilating orifice facing an operative lung or lobe thereof. For example, the distal end is inserted into a patient's right mainstem bronchus so that the ventilating orifice 216 is facing the patient's left mainstem bronchus. As another example, the distal end is inserted into a patient's left lung lower lobe bronchus so that the ventilating orifice 216 is facing the left lung upper lobe bronchus and another ventilating orifice 516 is facing the right mainstem bronchus. Thus, the distal end of the main tube is inserted into the bronchus of a ventilating lobe of a lung of the patient so that the ventilating orifice faces a bronchus of a different, operative lobe of a lung of the patient.

In step 607, one or more bronchial cuffs or a tracheal cuff or both are inflated. For example, tracheal cuff 240 and bronchial cuff 242 are inflated using corresponding pilot balloons to regulate the volume inflated. As another example, bronchial cuffs 242 and 540 are inflated using corresponding pilot balloons to regulate the volume inflated. Thus, step 607 includes, after inserting the distal end of the main tube, inflating at least one of an inflatable bronchial cuff disposed between the distal end of the main tube and the ventilating orifice or an inflatable tracheal cuff disposed between the proximal end of the main tube and the ventilating orifice. In embodiments without an inflatable cuff, or embodiments in which the outer diameter matches the inner diameter of the target bronchi, step 607 is omitted.

In step 609, the advanced SLV ETT is connected to ventilation equipment. For example, the ventilation adaptor 212 is connected to a pump or ventilation circuit for gas supply or suction or both. Thus, the proximal end of the main tube is connected to a ventilation source. In step 611, the ventilation equipment, e.g., a ventilation circuit is operated for gas supply or suction or both.

In step 613 the inner sleeve is moved to at least partially block the ventilating orifice facing the operative lung or lobe thereof. For example, an external structure, such as a handle or ring, is operated to position the inner sleeve in a second position to close the ventilating orifice in whole or in part. In some example embodiments, ring 230 is pushed toward the distal end of the main tube or ring 330 is rotated. As a result of step 613, the operative lung or lobe thereof becomes deflated. Thus, step 613 includes moving the sleeve to the second position or some intermediate position. In some embodiments, step 613 includes moving an external structure at the proximal end of the main tube, wherein the external structure is connected to the sleeve by a connecting element and is configured to move the sleeve between the first position and the second position.

In step 615, some procedure is performed on or in the vicinity of the operative lung or lobe thereof.

In step 617 the sleeve is moved to a position to at least partially ventilate the operative lung or lobe thereof, e.g. to suction or reflate the lung or lobe thereof. For example, in some embodiments, an external structure, such as a ring or handle, is moved to retract or rotate the inner sleeve, to the first position or to an intermediate position.

In step 619, the advance SLV ETT is removed from the patient; and the process ends.

As can be seen by the apparatus and method above, the advanced SLV ETT represents a novel design for single lung or lobe ventilation that may be applied even to small children.

4. References

The entire contents of each of the following references are hereby incorporated by reference as if fully set forth herein except for terminology that is inconsistent with that used herein.

1. Taylor C, Subaiya L, Corsino D. Pediatric cuffed endotracheal tubes: An evolution of care. Oschner J. 2011;11(1):52-6.
2. Campbell C, Viswanathan S, Riopelle J M, Naraghi M. Manufacturing defect in a double-lumen tube. Anesth Analg 1991;73:825-6]
3. Perel A, Katzenelson R, Klein E, Cotev S. Collapse of endotra-cheatubes due to overinflation of high-compliance cuffs. Anesth Analg 1977;56:731-3.
4. Hammer G B , Brodsky J B, Redpath J, Cannon W B: The Univent tube for single lung ventilation in children. Pediatr Anesth 1998;8:55-57.
5. Hammer G B, Harrison T K, Vricella L A, Black M D, Krane E J: Single lung ventilation in children using a new pediatric bronchial blocker. Pediatric Anesthesia 2002;12:69-72.

5. Alternatives and extensions

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. An apparatus for single lung ventilation, comprising:
   a hollow main tube with outer diameter sized to fit inside a bronchus of a patient and a length sufficient for a distal end of the main tube to reach a first side bronchus from a proximal end configured to be located in a vicinity of a mouth of the patient, wherein the hollow main tube has a ventilating orifice separated from the distal end at a location that corresponds to a different second side bronchus;
   a hollow tubular sleeve moveably disposed inside and longitudinally aligned with the main tube, the sleeve being configured to move, in a longitudinal direction, between a first position and a second position while remaining disposed inside the main tube, wherein the sleeve does not block the ventilating orifice while in the first position and does block the ventilating orifice while in the second position; and
   an outer ring coupled to, and disposed near, the proximal end of the main tube, the outer ring being configured to facilitate movement of the sleeve relative to the main tube.
2. An apparatus as recited in claim 1, wherein an inner diameter of the sleeve is greater than 50% of the outer diameter of the main tube.
3. An apparatus as recited in claim 1, wherein an inner diameter of the sleeve is greater than about 80% of the outer diameter of the main tube.
4. An apparatus as recited in claim 1, wherein the sleeve is displaced longitudinally toward the distal end in the second position compared to the first position.
5. An apparatus as recited in claim 1, wherein the sleeve is rotated in the second position compared to the first position.
6. An apparatus as recited in claim 1, wherein the sleeve is further configured to be positioned in a third position that partially blocks the ventilating orifice.
7. An apparatus as recited in claim 1, wherein the sleeve is configured to form an airtight seal at ventilating pressures with the main tube surrounding the ventilating orifice when the sleeve is in the second position.
8. An apparatus as recited in claim 1, further comprising a bronchial cuff disposed on the main tube between the distal end and the ventilating orifice.
9. An apparatus as recited in claim 8, wherein the bronchial cuff is inflatable.
10. An apparatus as recited in claim 1, further comprising a tracheal cuff disposed on the main tube between the proximal end and the ventilating orifice.
11. An apparatus as recited in claim 10, wherein the tracheal cuff is inflatable.
12. An apparatus as recited in claim 1, further comprising an adaptor affixed to the proximal end of the main tube, wherein the adaptor is configured for attachment to a ventilation source.
13. An apparatus as recited in claim 1, wherein the main tube inner diameter is selected from a group of diameters comprising: 3.5 mm, 4.0 mm, 4.5 mm, 5.0 mm, 5.5 mm, 6.0 mm, 6.5 mm, 7.0 mm, 7.5 mm, 8.0 mm, 8.5 mm and 9.0 mm.
14. The apparatus of claim 1, further comprising:
   a connector attached to the sleeve, a portion of the connector being configured to pass through a slit in the outer ring and extend through the outer ring.
15. The apparatus of claim 1, further comprising:
   a connector attached to the sleeve, the connector including two extensions, each extension being configured to protrude through a separate slit in the outer ring, wherein movement of the one or both extensions within their respective slit facilitates movement of the sleeve relative to the main tube.
16. The apparatus of claim 15, wherein at least one of the slits includes a plurality of notches that engage the extension protruding therefrom and inhibit movement of the extension within the slit.
17. The apparatus of claim 16, wherein movement of the one or both extensions into a notch of the plurality of notches by an operator provides tactile feedback to the operator.
18. A method for single lung ventilation, comprising:
   selecting an apparatus comprising:
      a hollow main tube with outer diameter sized to fit inside a bronchus of a patient and a length sufficient for a distal end of the main tube to reach a first side bronchus from a proximal end configured to be located in a vicinity of a mouth of the patient, wherein the hollow main tube has a ventilating orifice separated from the distal end at a location that corresponds to a different second side bronchus; and
      a hollow tubular sleeve moveably disposed inside, and longitudinally aligned with, the main tube, the sleeve being configured to move, in a longitudinal direction, between a first position and a second position while remaining disposed inside the main tube, wherein the sleeve does not block the ventilating orifice while in the first position and does block the ventilating orifice while in the second position; and an outer ring coupled to, and disposed near, the proximal end of the main tube, the outer ring being configured to facilitate movement of the sleeve relative to the main tube;

causing the sleeve to be at the first position;

inserting the distal end of the main tube into the bronchus of a ventilating lobe of a lung of the patient so that the ventilating orifice faces a bronchus of a different, operative lobe of a lung of the patient;

connecting the proximal end of the main tube to a ventilation source; and using the outer ring to move the sleeve to the second position.

19. A method as recited in claim 18, further comprising, after inserting the distal end of the main tube, inflating at least one of an inflatable bronchial cuff disposed between the distal end of the main tube and the ventilating orifice or an inflatable tracheal cuff disposed between the proximal end of the main tube and the ventilating orifice.

20. A method as recited in claim 18, wherein moving the sleeve to the second position further comprises moving an external structure at the proximal end of the main tube, wherein the external structure is connected to the sleeve by a connecting element and is configured to move the sleeve between the first position and the second position.

21. The method of claim 18, wherein the apparatus further comprises a connector attached to the sleeve, a portion of the connector being configured to pass through a slit in the outer ring and wherein moving the sleeve to the second position further comprises moving the portion of the connector configured to pass through the slit within the slit.

22. The method of claim 18, wherein the apparatus further comprises a connector attached to the sleeve, the connector including two extensions, each extension being configured to protrude through a separate slit in the outer ring and wherein moving the sleeve to the second position further comprises moving one or both extensions within their respective slit.

23. The method of claim 22, wherein the at least one of the slits includes a plurality of notches that engage the extension protruding therefrom and inhibit movement of the extension within the slit and wherein moving the sleeve to the second position further comprises moving one or both extensions within their respective slit until the one or both extensions engages with its respective notch.

24. The method of claim 23, wherein movement of the one or both extensions into a notch of the plurality of notches by an operator provides tactile feedback to the operator.

* * * * *